United States Patent [19]

Ezer et al.

[11] Patent Number: 4,587,251
[45] Date of Patent: May 6, 1986

[54] INDOLO[2,3-A]QUINOLIZINE AND INDOLO[2,3-G]CYCLOPENT[A]INDOLIZINE DERIVATIVES, COMPOSITIONS AND METHODS EMPLOYING THEM FOR TREATING ULCERS

[75] Inventors: Elemer Ezer; László Szporny; György Hajós; Csaba Szántay; Tibor Keve; György Fekete; Gábor Megyeri; Tibor Ács; Hedvig Bölcskei, all of Budapest, Hungary

[73] Assignee: Richter Gedeon Vegyeszeti Gyar R.T., Budapest, Hungary

[21] Appl. No.: 625,071

[22] Filed: Jun. 27, 1984

[30] Foreign Application Priority Data

Jun. 29, 1983 [HU] Hungary ............... 2342/83

[51] Int. Cl.$^4$ ............... A61K 31/435; C07D 471/14; C07D 471/18
[52] U.S. Cl. ............... 514/281; 514/283; 546/43; 546/51; 546/112
[58] Field of Search ............... 546/43, 51; 514/281, 514/283

[56] References Cited

U.S. PATENT DOCUMENTS 3,542,799 11/1970 Shavel, Jr. et al. ............... 546/51
3,639,408 2/1972 Nagata et al. ............... 546/43

FOREIGN PATENT DOCUMENTS 2753730 6/1979 Fed. Rep. of Germany ........ 546/51

Primary Examiner—Nicholas S. Rizzo
Assistant Examiner—Diana G. Rivers
Attorney, Agent, or Firm—Karl F. Ross; Herbert Dubno

[57] ABSTRACT

The invention relates to new indolo[2,3-g]cyclopent[a]indolizine derivatives of the formulae (II)

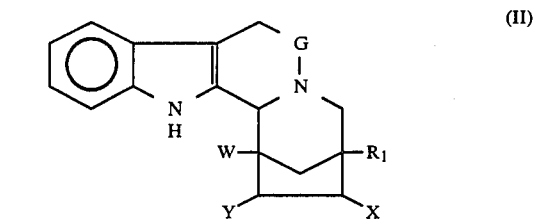

and/or (III)

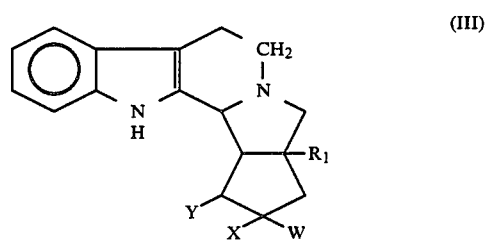

wherein
W is alkoxycarbonyl having from one to four carbon atoms in the alkoxy moiety or cyano,
$R_1$ is hydrogen or alkyl having from one to four carbon atoms,
G is a >$CH_2$ or >C=O group, and
X and Y each stands for hydrogen or together represent a C—C bond.

According to another aspect of the invention there is provided a process for the preparation of the above compounds, which are pharmaceutically active, in particular, possess valuable gastric acid secretion inhibiting activity. Pharmaceutical compositions containing compounds of the formulae (II) and/or (III) are also within the scope of the invention.

8 Claims, No Drawings

INDOLO[2,3-A]QUINOLIZINE AND INDOLO[2,3-G]CYCLOPENT[A]INDOLIZINE DERIVATIVES, COMPOSITIONS AND METHODS EMPLOYING THEM FOR TREATING ULCERS

The invention relates to new indolo[2,3-a]-quinolizine and indolo[2,3-g]cyclopent[a]indolizine derivatives. More particularly, the invention concerns new indolo[2,3-a]quinolizines of the formula (II)

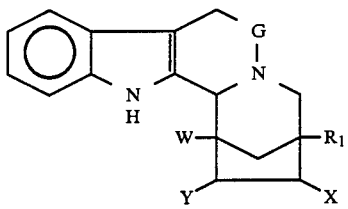

and new indolo[2,3-g]cyclopent[a]indolizines of the formula (III)

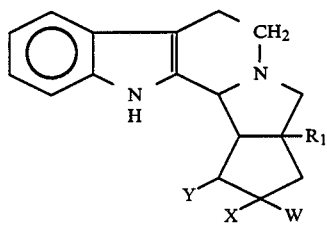

wherein
W is alkoxycarbonyl having from one to four carbon atoms in the alkoxy moiety or cyano,
$R_1$ is hydrogen or alkyl having from one to four carbon atoms,
G is a $<CH_2$ or $<C=O$ group, and
X and Y each stand for hydrogen or together represent a C—C bond.

According to another aspect of the invention there is provided a process for the preparation of the above compounds. Compounds of the formulae (II) and (III) are biologically active, in particular possess valuable gastric acid secretion inhibiting activity. Pharmaceutical compositions containing them as active ingredient are also within the scope of the invention.

According to the invention compounds of the formulae (II) and/or (III) are prepared starting from compounds of the formula (I)

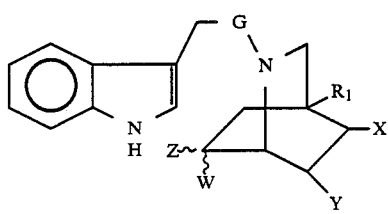

in which W, $R_1$, G, X and Y are as defined above, and Z is halo.

To prepare compounds of the formulae (II) and/or (III), in which G is a $<CH_2$ group, compounds of the formula (I), in which G stands for $<CH_2$, W, $R_1$, X, Y and Z have the same meanings as defined above, are heated in an organic solvent, and if desired, the obtained mixture of the compounds of the formulae (II) and (III) is separated, and/or compounds of the formula (II) are converted into the corresponding compounds of the formula (III), and/or if desired, the compounds, in which X and Y together represent a C—C bond, are saturated by catalytic hydrogenation.

Compounds of the formula (II), in which G represents a $<C=O$ group, W is a $C_{1-4}$ alkoxycarbonyl group, $R_1$ is hydrogen, X and Y are as given above, are prepared by reacting the corresponding compounds of the formula (I), in which G, W, $R_1$, X, Y and Z have the same meanings as defined directly above, with a complexing agent, in an organic solvent, under anhydrous conditions, and if desired, the compounds obtained, in which X and Y together represent a C—C bound, are saturated by catalytic hydrogenation.

In the above formulae as an alkoxycarbonyl group having from one to 4 carbon atoms in the alkoxy moiety W may represent any straight or branched chain $C_{1-4}$ alkoxycarbonyl, e.g. methoxy, ethoxy, n- or isopropoxy, n-, iso- or tert.-butoxycarbonyl group.

$R_1$ may represent any straight chain or branched $C_{1-4}$ alkyl group, e.g. a methyl, ethyl, n-propyl, isopropyl, n-butyl, isobutyl or tert.-butyl group.

Z as a halo may stand for fluorine, chlorine, bromine or iodine.

Compounds of the formula (II) have an entirely new structure, there are no structurally related compounds known in the art.

A structure analogue of the compounds of the formula (III) has been prepared by Winterfeldt et al. [Angew. Chem. 89(12), 916–17 (1977)] as a key intermediate of the synthesis of eburnamonine [Chemische Berichte 112(5), 1879–1888, 1889–1901, 1902–1912 (1979) and 114(5) 1932–1937 (1981)].

Cyclopent[1,2]indolizino[8,7-b]indole derivatives are also disclosed in Org. Mass. Spektrom. 15(10),544 (1980).

According to one aspect of the invention an N-[(3-indolyl)-ethyl]-2-azabicyclo[2.2.2]octane derivative of the formula (I), in which G is a $<CH_2$ group, which may be prepared according to our co-pending Hungarian patent application No. 2343/83, and according to our co-pending U.S. Pat. application, is heated in an organic solvent to yield a mixture of the corresponding compounds of the formulae (II) and (III). As an organic solvent, preferably polar protic solvents are used. At lower temperatures, after a short heating compounds of the formula (II) are obtained, which may then be converted into the corresponding thermodynamically more stable compounds of the formula (III) by a longer heating at higher temperature.

Compounds of the formulae (II) and (III) may be separated from each other by column chromatography, and after isolation, compounds of the formula (II) may be converted into the corresponding compounds of the formula (III).

Under appropriate reaction conditions compounds of the formula (I) can directly be converted into essentially pure compounds of the formula (III), i.e. the amount of the compounds of formula (II) formed can be minimized.

The separation of the compounds of the formulae (II) and (III) is preferably carried out by column chromatography. The unreacted starting substance is separated from the mixture of the compounds of formulae (II) and (III) preferably on a Kieselgel 60 column, by gradient elution technique, and the compounds of the formulae (II) and (III) are then separated from each other on an $Al_2O_3$ column, again by gradient elution technique.

As a polar protic solvent preferably alcohols having one to four carbon atoms or diethylene glycol are employed.

Compounds of the formula (I), in which G represents a <C=O group, due to their reduced reactivity, cannot be converted into the corresponding compounds of the formulae (II) and (III) thermically, instead they are heated in the presence of a complexing agent, preferably silver tetrafluoroborate or silver hexafluoroantimonate, in apolar aprotic solvents, under anhydrous conditions to yield the corresponding compounds of the formula (II). The compounds of the formula (II) obtained by this reaction cannot be further transformed into compounds of the formula (III).

In the reaction performed in the presence of complexing agents as an apolar aprotic organic solvent preferably halogenated aliphatic hydrocarbons such as dichloromethane; aromatic hydrocarbons, e.g. benzene or toluene; or nitrobenzene are employed.

If desired, the compounds of the formula (II) or (III), in which X and Y together form a C—C bond, can be saturated in a known manner, by catalytic hydrogenation. Catalytic hydrogenation is preferably carried out in the presence of a palladium-on-charcoal catalyst.

According to a further feature of the present invention there are provided pharmaceutical compositions, comprising, as active ingredient, a compound of the formula (II) and/or (III) as hereinbefore defined, in association with a pharmaceutical carrier or excipient.

The invention is elucidated in detail by the aid of the following non-limiting Examples.

EXAMPLE 1

Methyl 1,3-vinylene-1,3,4,6,7,12b-hexahydro-2H,12H-indolo[2,3-a]quinolizinyl-1-carboxylate 1 g. ($3.24 \times 10^{-3}$ moles) of N-[(3-indolyl)-ethyl]-7-chloro-7-methoxycarbonyl-2-azabicyclo[2.2.2]oct-5-ene is dissolved in 10 ml. of tert.-butanol and the solution is stirred at boiling temperature (83° C.) for 24 hours. It is the evaporated in vacuo and chromatographed on a Kieselgel 60 column, using a 8:4:2 mixture of toluene, chloroform and ethanol as eluent. The obtained mixture of the compounds of the formulae (II) and (III) is subjected to column chromatography on an $Al_2O_3$ column, using a 1:1 mixture of ethyl acetate and chloroform as eluent. 0.25 g. ($9.2 \times 10^{-4}$ moles) of the title compound are obtained as oil which solidifies.

Yield: 28.4%.

IR(KBr): 3340 (indole NH), 1720 (C=O) cm$^{-1}$ $^1$H NMR (CDCl$_3$): 7.55–7.0 (m, 4H, aromatic H-s) 6.32–6.05 (d, 2H, olefin H-s) 3.95 (br, 3H, OCH$_3$) ppm.

$^{13}$C NMR (CDCl$_3$): C$_1$ (57.59s), C$_2$ (40.24t), C$_3$ (40.24d), C$_4$ (45.41t), C$_6$ (50.29t), C$_7$ (17.54t), C$_{7a}$ (110.74s), C$_{7b}$(127.2s), C$_8$(118.02d), C$_9$ (121.83d), C$_{10}$ (119.37d), C$_{11}$ (111.24d), C$_{11a}$(131.76s), C C$_{12a}$ (136.01s), C$_{12b}$(55.09d), C$_{13}$(134.95d), C$_{14}$ (132.8d) ppm.

MS m/e/80° C.: 308(10, M), 243 (4.4), 241 (5.0), 220(46.0), 200(3.0), 184 (35.0), 256(17.0)%.

EXAMPLE 2

Methyl 3a,4,6,7,12b,12c-hexahydro-3H,12H-indolo[2,3-g]-cyclopent[a]indolizine-2-carboxylate 1 g. ($3.24 \times 10^{-3}$ moles) of N-[(3-indolyl)-ethyl]-7-chloro-7-methoxycarbonyl-2-azabicyclo[2.2.2]oct-5-ene is dissolved in 10 ml. of n-butanol and the solution is stirred at 110° C. for 5 hours. The progress of the reaction is monitored by thin layer chromatography. The reaction mixture is evaporated in vacuo, and chromatographed on a Kieselgel 60 column, using a 8:4:2 mixture of toluene, chloroform and ethanol as eluent.

Yield: 0.47 g. (53%)

IR(KBr): 3320 (indole NH), 1720 (C=O) cm$^{-1}$ $^1$H NMR (CDCl$_3$): 7.55–7.0 (m, 4H, aromatic H-s) 6.25 (d, 1H, olefine) 3.95 (s, 3H, OCH$_3$) ppm $^{13}$C NMR (CDCl$_3$): C$_1$ (149.8d), C$_2$ (112.7s), C$_3$ (39.6t), C$_{3a}$ (41.4d), C$_4$ (45.8t), C$_6$ (50.29t), C$_7$ (17.54t), C$_{7a}$ (110.7s), C$_{7b}$ (127.2s), C$_8$ (118.02d), C$_9$ (121.83d), C$_{10}$ (119.37d), C$_{11}$ (111.2d), C$_{11a}$ (131.76s), C$_{12a}$ (136.02s), C$_{12b}$ (62.6d), C$_{12c}$ (56.8d) ppm.

MS m/e: 308 (10 M), 243 (1.4), 241 (1.5), 220 (2.8), 200 (4.8), 184 (100), 169 (3.9)%.

EXAMPLE 3

Methyl 3a,4,6,7,12b,12c-hexahydro-3H,12H-indolo[2,3-g]cyclopent[a]indolizine-2-carboxylate 0.25 g. of methyl 1,3-vinylene-1,3,4,6,7,12b-hexahydro-2H,12H-indolo[2,3-a]quinolizinyl-1-carboxylate prepared in Example 1 [compound of formula (II)] are dissolved in 12 ml. of toluene and boiled (111° C.) for 3 hours. The end-product is isolated from the reaction mixture as described in Example 2. The physical characteristics of the product obtained are identical with those given in Example 2.

Yield: 0.19 g. (76%)

EXAMPLE 4

2-Cyano-3a,4,6,7,12b,12c-hexahydro-3H,12H-indolo[2,3-g]cyclopent[a]indolizine 1 g. ($3.2 \times 10^{-3}$ moles) of N-[(3-indolyl)-ethyl]-7-chloro-7-cyano-2-azabicyclo[2.2.2]oct-5-ene is dissolved in 1.5 ml. of diethylene glycol at 80° C., and the solution is stirred at 160° C. for 20 minutes. The progress of the reaction is monitored by thin layer chromatography. The reaction mixture is cooled to 20° C., diluted with 15 ml. of acetone and the product obtained is isolated in a crystalline form (melting point: 234° to 237° C.).

Yield: 0.2 g. (22%)

IR (KBr): 3320 (indole NH), 2230 (CN) cm$^{-1}$ $^1$H NMR (CDCl$_3$+DMSO): 7.77–7.1 (m, 4H, aromatic H-s) 6.85 (d, 1H, olefin) 4.1 (d, 1H, N—CH) 3.65 (m, 1H, CH beside olefin) ppm.

$^{13}$C NMR (CDCl$_3$+DMSO): C$_1$(149.8d), C$_2$(114.8s), C$_3$ (39.6t), C$_{3a}$ (41.4d), C$_4$ (45.8t), C$_6$ (57.1d), C$_7$ (17.6t), C$_{7a}$ (106.77s), C$_{7b}$ (126.97s), C$_8$ (117.91d), C$_9$ (121.07d), C$_{10}$ (118.72d), C$_{11}$ (110.99d), C$_{11a}$ (133.54s), C$_{12a}$ (136.37s), C$_{12b}$ (62.6d), C$_{12c}$ (56.8d) ppm.

MS m/e: 276 (10.1), 275 (23 M), 274 (6), 185 (23), 184 (100), 183 (11), 169 (7)%.

EXAMPLE 5

Methyl 3-ethyl-3a,4,6,7,12b,12c-hexahydro-3H,12H-indolo[2,3-g]cyclopent[a]indolizine-2-carboxylate 1 g. of N-[3-indolyl)-ethyl]-7-chloro-7-methoxycarbonyl-4-ethyl-2-azabicyclo[2.2.2]oct-5-ene is dissolved in 20 ml. of methanol, and the solution is refluxed in nitrogen atmosphere. The progress of the reaction is monitored by thin layer chromatography. When the total amount of the starting material is used up, the reaction mixture is evaporated in vacuo, and the oily product is chromatographed on a Kieselgel 60 chromatographic column, using a 8:4:2 mixture of benzene, chloroform and ethanol as eluent. The product is crystallized from a 96% ethanolic solution of sulfuric acid in the form of its sulfate salt.

Melting point: 285° to 288° C.
Yield: 0.3 g. (37%).
IR (KBr): 3340 (indole NH), 1720 (C=O) cm$^{-1}$
$^1$H NMR (CDCl$_3$): 7.65–7.0 (m, 4H, aromatic H-s) 6.95 (d, 1H, olefin) 3.8 (d, 1H, CH—N) 0.9 (t, 3H, CH$_2$—CH$_3$) ppm
MS m/e: 336 (M 13), 335 (2.3), 321 (2.9), 305 (46), 184 (100), 169 (5.2)%

EXAMPLE 6

2-Cyano-3-ethyl-3a,4,6,7,12b,12c-hexahydro-3H,12H-indolo[2,3-g]cyclopent[a]indolizine 1 g. (2.85×10$^{-3}$ moles) of N-[(3-indolyl)ethyl]-7-chloro-7-cyano-4-ethyl-2-azabicyclo[2.2.2]-oct-5-ene is dissolved in 20 ml. of n-butanol, and the solution is refluxed for 6 hours. The progress of the reaction is monitored by thin layer chromatography. When the total amount of the starting substance is used up, the mixture is evaporated in vacuo, and the obtained oily product is subjected to column chromatography as described in Example 5.

Yield: 0.2 g. (23%)
IR (KBr): 3340 (indole NH), 2230 (CN) cm$^{-1}$.
$^1$H NMR (CDCl$_3$): 7.78–7.13 (m, 4H, olefin H-s) 6.9 (d, 1H, olefin) 3.75 (d, 1H, CH—N) 0.9 (t, 3H, CH$_2$—CH$_3$) ppm.
MS m/e: 303 (12M), 302 (2.5), 288 (2.7), 272 (48), 184 (100)%

EXAMPLE 7

Methyl 1,3-ethylene-1,3,4,6,7,12b-hexahydro-2H,12H-indolo[2,3-a]quinolizinyl-1-carboxylate 0.1 g. (2.88×10$^{-4}$ moles) of N-[(3-indolyl)-ethyl]-6-chloro-6-methoxycarbonyl-2-azabicyclo[2.2.2]octane are dissolved in 1 ml. of diethylene glycol at 190° C., and the solution is stirred for 20 minutes. The product obtained is separated by column chromatography as described in Example 5 (eluent: a 8:4:2 mixture of toluene, chloroform and ethanol), isolating the product obtained at R$_f$=0.62.

Melting point: 148° to 151° C.
Yield: 0.03 g. (33.5%).
IR (KBr): 3320 (indole NH), 1720 (C=O) cm$^{-1}$.
$^1$H NMR (CDCl$_3$): 7.55–7.0 (m, 4H, aromatic H-s) 3.85 (s, 3H, OCH$_3$) ppm.
$^{13}$C NMR (CDCl$_3$): C$_1$ (52.83s, 34.57t), C$_3$ (36.12d), C$_4$ (51.94t), C$_6$ (50.61t), (17.01t), C$_{7a}$ (109.65s), C$_{7b}$ (127.39s), C$_8$ (118.02d), C$_9$ (121.66d), C$_{10}$ (119.37d), C$_{11}$ (111.24d), C$_{11a}$ (132.7a), C$_{12a}$ (135.95s), C$_{12b}$ (t1.55d), C$_{13}$ (28.65t), C$_{14}$ (36.56t) ppm
MS m/e: 310 (58. M), 309 (100), 295 (2), 279 (3.8), 259 (0.5), 251 (2) 239 (1.5), 223 (1.9), 211 (15), 185 (7), 187 (7), 182 (10)%.

EXAMPLE 8

Methyl 1,3-vinylene-1,3,4,6,7,12b-hexahydro-2H,12H-indolo[2,3-a]quinolizine-6-one-1-carboxylate 1 g. (2.5×10$^{-3}$ moles) of N-[(3-indolyl)-acetyl]-7-bromo-7-methoxycarbonyl-2-azabicyclo[2.2.2]oct-5-ene is dissolved in 40 ml. of dry dichloromethane. To this solution a solution of silver tetrafluoroborate in benzene is added under continuous stirring, and the mixture is stirred at room temperature. The progress of the reaction is monitored by thin layer chromatography. The inorganic compounds are eliminated from the reaction mixture with 5 ml. of a saturated sodium bicarbonate solution, the organic phase is dried, evaporated in vacuo, and the components are separated by column chromatography as described in Example 5 and isolated as a colorless oil.

IR (film): 3400 (indol NH), 1720 (C+O), 1600 (N—C=O) cm$^{-1}$.
$^1$H NMR (CDCl$_3$): 7.55–7.07m, 4H, aromatic H-s) 6.32–5.81 (d, m, 2H, olefin) 5.23–4.71 (t and 2xm, 2H, N—CH$_2$—) 3.81 (s, 3H, OCH$_3$) ppm
$^{13}$C NMR (CDCl$_3$): C$_1$ (60.56s, 43.19t), C$_3$ (39.54d), C$_4$ (49.90t), C$_6$ (169.92s), C$_7$ (29.25t), C$_{7a}$ (106.79s), C$_{7b}$ (126.69s), C$_8$ (118.45d), C$_9$ (122.88d), C$_{10}$ (119.83d), C$_{11}$ (116.16d), C$_{11a}$ (125.29s), C$_{12a}$ (136.59s), C$_{12b}$ (59.25d), C$_{13}$ (136.97d), C$_{14}$ (130.05d) ppm.
MS m/e: 322 (45.M), 305 (6), 291 (4), 198 (80), 185 (10), 184 (52), 170 (100), 169 (86), 115 (11)%.

EXAMPLE 9

Methyl 1,3-ethylene-1,3,4,6,7,12b-hexahydro-2H,12H-indolo[2,3-a]quinolizine-6-one-1-carboxylate 0.45 g. (1.26×10$^{-3}$ moles) of N-[(3-indolyl)-acetyl]-6-chloro-6—methoxycarbonyl-2-azabicyclo[2.2.2]-octane are reacted with silver tetrafluoroborate. Furtheron the procedure described in Example 8 is followed. The end-product is isolated as a colorless oil.

IR (film): 3400 (NH), 1700 (C=O), 1600 (N—C=O)
$^1$H NMR (CDCl$_3$): C$_1$ (57.89s), C$_2$ (31.88t), C$_3$ (36.09d), C$_4$ (50.23t), C$_6$ (168.57s), C$_7$ (29.19t), C$_{7a}$ (107.00s), C$_{7b}$ (126.31s), C$_8$ (118.43d), C$_9$ (122.87d), C$_{10}$ (119.94d), C$_{11}$ (110.90d), C$_{11a}$ (125.29s), C$_{12a}$ (136.85s), C$_{12b}$ (63.77d), C$_{13}$ (31.15t), C$_{14}$ (32.92t) ppm
MS m/e: 324 (100, M), 307 (24), 293 (5.3), 292 (4.3), (6.5), 225 (9.4), 199 (11), 198 (15), 184 (8.2), 171 (47)%.

EXAMPLE 10

2-Cyano-1,2,3a,4,6,7,12b,12c-octahydro-3H,12H-indolo-[2,3-g]cyclopent[a]indolizine 0.27 g. (1×10$^{-3}$ moles) of 2-cyano-3a,4,6,7,12b-hexahydro-3H,12H-indolo[2,3-g]cyclopent[a]indolizine are dissolved in 5 ml. of methyl alcohol, and this solution is added to a prehydrogenated solution of 0.05 g. of a 10% palladium-on-charcoal catalyst in 2 ml. of methanol, and hydrogen gas is bubbled through the reaction mixture under vigorous stirring. The progress of the reaction is followed by thin layer chromatography, the catalyst is filtered off, washed with methanol and the combined alcoholic phases are evaporated in vacuo to yield 0.25 g. of an oily product.

IR (KBr): 3320 (indole NH), 2230 (CN) cm$^{-1}$.

$^1$H NMR (CDCl$_3$): 7.65–7.05 (m, 4H, aromatic H-s) 4.1 (d, 1H, N—CH) ppm $^{13}$C NMR (CDCl$_3$): C$_1$ (40.07t), C$_2$ (42.78d), C$_3$ (39.65t), C$_{3a}$ (41.37d), C$_4$ (45.85t), C$_6$ (50.29t), C$_7$ (17.57t), C$_{7a}$ (110.7s), C$_{7b}$ (127.2s), C$_8$ (118.02d), C$_9$ (121.83d), C$_{10}$ (119.37d), C$_{11}$ (111.2d), C$_{11a}$ (137.72s), C$_{12a}$ (136.15s), C$_{12b}$ (62.47d), C$_{12c}$ (56.78d) ppm MS m/e: 277 (58, M), 276 (66), 252 (2.9), 251 (3), 209 (7.5), 184 (100), 169 (11)%

EXAMPLE 11

Methyl 1,2,3a,4,6,7,12b,12c-octahydro-3H,12H-indolo-[2,3-g]cyclopent[a]indolizine-2-carboxylate 0.052 g. of methyl 3a,4,6,7,12b,12c-hexahydro-3H,12H-indolo[2,3-g]cyclopent[a]indolizine-2-carboxylate are reduced as described in Example 10. The obtained product is isolated as an oil.

Yield: 0.048 g. (96%).

IR (KBr): 3320 (indole, NH), 1720 (C=O) cm$^{-1}$.

$^1$H NMR (CDCl$_3$): 7.55–7.05 (m, 4H, aromatic, H-s) 3.95 (s, 3H, OCH$_3$) ppm.

$^{13}$C NMR (CDCl$_3$): C$_1$ (39.6t), C$_2$ (43.2d), C$_3$ (39.85t), C$_{3a}$ (41.25d), C$_4$ (45.87t), C$_6$ (50.35d), C$_7$ (17.54t), C$_{7a}$ (110.76s), C$_{7b}$ (127.23s), C$_8$ (118.12d), C$_9$ (121.83d), C$_{10}$ (119.37d), C$_{11}$ (111.2d), C$_{11a}$ (131.76s), C$_{12a}$ (136.02s), C$_{12b}$ (62.45d), C$_{12c}$ (56.68d) ppm.

EXAMPLE 12

Methyl 3-ethyl-1,2,3a,4,6,7,12b,12c-octahydro-3H,12H-indolo[2,3-a]cyclopent[a]indolizine-2-carboxylate.

Essentially the procedure described in Example 10 is followed except that as starting material methyl 3-ethyl-3a,4,6,7,12b,12c-hexahydro-3H,12H-indolo[2,3-g]cyclopent-[a]indolizine-2-carboxylate is employed.

IR (film): 3340 (indole NH), 1720 (C=O) cm$^{-1}$.

$^1$H NMR (CDCl$_3$): 7.75–7.13 (m, 4H, aromatic H-s) 3.85 (d, 1H, CH—N) 0.9 (t, 3H, CH$_2$-CH$_3$) ppm.

MS m/e: 338 (90M), 337 (100), 239 (9), 185 (14), 184 (22), 170 (16), 169 (31)%.

EXAMPLE 13

2-Cyano-3-ethyl-1,2,3a,4,6,7,12b,12c-octahydro-3H,12H-indolo[2,3-g]cyclopent[a]indolizine Essentially following the procedure described in Example 10 but starting from 2-cyano-3-ethyl-3a,4,6,7,12b,12c-hexahydro-3H,12H-indolo[2,3-g]cyclopent[a]indolizine the title compound is obtained.

IR (film): 3340 (indole NH), 2230 (CN) cm$^{-1}$.

$^1$H NMR (CDCl$_3$): 7.75–7.1 (m, 4H, aromatic H-s) 3.70 (d, 1H, CH—N) 0.9 (t, 3H, CH$_2$—CH$_3$) ppm.

EXAMPLE 14

Methyl 1,3-ethylene-1,3,4,6,7,12b-hexahydro-2H,12H-indolo[2,3-a]quinolizinyl-1-carboxylate Essentially following the procedure described in Example 10 but starting from methyl 1,3-vinylene-1,3,4,6,7,12b-hexahydro-2H,12H-indolo[2,3-a]quinolizinyl-1-carboxylate the title compound is obtained.

The following examples are directed to the preparation of the starting materials of the Formula (I).

PREPARATION EXAMPLE 1

2-Benzyloxycarbonyl-4-ethyl-7-chloro-7-methoxycarbonyl-2-azabicyclo[2.2.2]oct-5-ene 21.4 g. (0.2 moles) of 3-ethyl-pyridine are dissolved in 250 ml. of absolute methanol. To the solution 7.5 g. (0.2 moles) of powdered sodium tetrahydroborate are slowly added below −65° C. under vigorous stirring in an argon atmosphere, followed by the addition of 28.8 ml. (34.1 g., 0.2 moles) of benzyl chloroformate. The reaction is strongly exothermic. When the addition is complete, the reaction mixture is stirred for an additional hour, whereupon it is carefully heated up to room temperature. The reaction mixture is evaporated in vacuo. The evaporation residue is dissolved in 200 ml. of ether and washed with 100 ml. of water. The aqueous phase is extracted with two additional 100-ml. portions of ether. The combined ethereal phases are washed with 20 ml. of a 1% aqueous acetic acid solution. The pH of the aqueous solution is about 5–6 after the extraction. The ethereal phase is dried over magnesium sulfate, and evaporated in vacuo. The evaporation residue is a mixture of N-benzyloxycarbonyl-1,2-, 1,4- and 1,6-3-ethyl-dihydropyridine isomers.

UV spectrum (methanolic solution):

$\lambda_{max}$=305 nm 1,2- and 1,6-3-ethyl-dihydropyridine $\lambda_{max}$=260–270 nm unreacted 3-ethyl-pyridine $\lambda_{max}$=230–240 nm 1,4-dihydropyridine.

The evaporation residue weighs 36.7 g. (0.153 moles).

IR spectrum: 1700 cm$^{-1}$=N—C=O; 1470 cm$^{-1}$ phenyl; 1100 cm$^{-1}$ C—O—C; 700 cm$^{-1}$; phenyl.

t.l.c. (Kieselgel 60 F$_{154}$, eluent: 10:1 mixture of benzene and acetone, development: in UV light of 254 nm or iodine vapor): R$_f$=0.84 (1,2 and 1,6 isomers).

The evaporation residue is dissolved in 150 ml. of absolute acetonitrile, and 24.4 g. (0.194) of 2-chloroacrylic acid chloride and 0.1 g. of hydroquinone are added to the solution. The completion of the cycloaddition is shown by the disappearance of the $\lambda_{max}$=305 nm peak in the UV spectrum. Thereafter, 150 ml. of absolute methanol are added to the reaction mixture, which is then stirred at room temperature for three hours. The pH of the acidic solution is adjusted to 8–9 by addition of triethyl amine under cooling, and it is then evaporated in vacuo. The evaporation residue is dissolved in 100 ml. of benzene, and washed with 50 ml. of water. The benzene phase is dried over magnesium sulfate, filtered and evaporated in vacuo. 59.9 g. of an oily product are obtained, which is then chromatographed on a Kieselgel 60 (0.063–0.2 mm.) column by using a 10:1 mixture of benzene and acetone as an eluent.

Yield: 19.3 g. (35% based on 3-ethyl-pyridine).

IR spectrum (film): 1700 cm$^{-1}$=N—O; 1470 cm$^{-1}$ phenyl; 1100 cm$^{-1}$ C—O—C; 700 cm$^{-1}$ phenyl.

t.l.c. (Kieselgel 60 F$_{254}$, eluent: a 10:1 mixture of benzene and acetone, development: in UV light of 254 nm or in iodine vapor): R$_f$=0.85.

PREPARATION EXAMPLE 2

2-Benzyloxycarbonyl-4-ethyl-7-chloro-7-cyano-2-azabicyclo-[2.2.2]oct-5-ene 50 g. (0.2 moles) of 3-ethyl-(N-benzyloxycarbonyl)-1,2-dihydropyridine, contaminated with the 1,4- and 1,6-isomers, are prepared as described in Preparation Example 1. It is then dissolved in 60 g. (0.69 moles) of 2-chloroacryl nitrile together eith 1 g. of hydroquinone. The reaction mixture is protected from light and stirred on an oil bath of 70° C. for 70 hours. The completion of the cyclo-addition is shown by the disappearance of the $\lambda_{max}=305$ nm peak in the UV spectrum. The reaction mixture is evaporated in vacuo, on a water bath of 50°–60° C., the residual oil is dissolved in 50 ml. of benzene, washed with 50 ml. of water and subsequently with two 50-ml. portions of benzene. The benzene phase is dried over magnesium sulfate and evaporated in vacuo to yield an oily residue. It is the column chromatographed on a 30-fold amount of Kieselgel 60 (0.063–0.2 nm), using a 10:1 mixture of benzene and acetone as an eluent. The $R_f>0.75$ fractions are combined, evaporated and column chromatogrpahed again on a 40-fold amount of a Kieselgel 60 (0.063–0.2 nm), with a 1:1 mixture of benzene and chloroform as an eluent. The product obtained at $R_f=0.56$ is isolated.

Yield: 8.5 g. (0.0257 moles), 13% based on the starting 3-ethyl-pyridine.

t.l.c. (Kieselgel 60 $F_{254}$, eluent: 10:1 benzene/acetone, $R_f=0.812$; 1:1 benzene/chloroform $R_f=0.56$; development in iodine vapor or in UV light of 254 nm.

IR spectrum (film) $cm^{-1}$: 2300—CN; 1700 N—C=O; 1470 Ph; 700 Ph.

NMR spectrum (CDCl$_3$) ppm: 7.3 (5 aromatic H-s); 6.3–6.4 (d, $H_1^5+H_1^6$); 5.15 (S benzyl —CH$_2$—); 5.05 (d, $H_1^1$).

PREPARATION EXAMPLE 3

N-Benzyloxycarbonyl-7-chloro-7-methoxycarbonyl-2-azabicyclo[2.2.2]oct-5-ene 118.5 g. (1.5 moles) of absolute pyridine are dissolved in 1000 ml. of absolute methanol, whereupon 57 g. (1.5 moles) of powdered sodium borohydride are carefully added at a temperature below −65° C., followed by the addition of 248 ml. (298 g., 1.75 moles) of benzyl chloroformate. The reaction is strongly exothermic. When the addition is complete, the mixture is stirred for an additional hour at −70° C., and is then carefully heated up to room temperature. The evaporation residue is dissolved in 400 ml. of ether, and washed with 400 ml. of water, 100 ml. of a 0.1 n aqueous hydrochloric acid solution and subsequently with two additional 100-ml. portions of water. The pH of the aqueous phase is about 5–6 after the extraction. The ethereal phase is dried over magnesium sulfate and evaporated. UV spectrum of the evaporation residue, containing a mixture of 1,2- and 1,4-dihydropyridine isomers in methanolic solution:

$\lambda_{max}=305$ nm 1,2-dihydropyridine,
$\lambda_{max}=260-270$ nm unreacted pyridine,
$\lambda_{max}=230-240$ nm 1,4-dihydropyridine.

The 248 g. of the evaporation residue obtained are dissolved in 700 ml. of acetonitrile, and 192 g. (1.54 moles) of 2-chloroacrylic acid chloride and 5 g. of hydroquinone are added. The completion of the cycloaddition is shown in the spectrum by the disappearance of the $\lambda_{max}=305$ nm peak. Thereafter 400 ml. of methanol are added to the mixture, which is allowed to stand at room temperature for three hours. The pH of the acidic solution is adjusted to 8–9 with triethyl amine, under cooling, and it is then evaporated. The evaporation residue is dissolved in 500 ml. of benzene and washed with 100 ml. of water. The benzene phase is dried over magnesium sulfate and evaporated. 442 g. of an oily product are obtained as an evaporation residue, which is chromatographed on a Kieselgel 60 (0.063–0.2 mm) column, using a 10:1 mixture of toluene and ethyl acetate as an eluent.

Yield: 95 g. (18.9%, 0.284 moles)
Melting point: 85° C.
t.l.c. (Kieselgel 60 plate, eluent: 10:1 benzene/ethyl acetate, development in iodine vapor): $R_f=0.6$ IR spectrum: 1720 $cm^{-1}$ ester C=O; 1690 $cm^{-1}$ lactame C=O.

NMR spectrum: 2.75 ppm (s-OCH$_3$), 5.2 ppm (s, benzyl —CH$_2$—), 6.3 ppm (m olefin H-s), 7.4 ppm (aromatic H-s).

PREPARATION EXAMPLE 4

N-Benzyloxycarbonyl-7-chloro-7-cyano-2-azabicyclo-[2.2.2]oct-5-ene

N-benzyloxycarbonyl-1,2-dihydropyridine prepared from 15.8 g. (0.2 moles) of pyridine as described in Preparation Example 3 are dissolved in 100 ml. of acetonitrile. 34 g. (0.4 moles) of α-chloro-acrylnitrile and 2 g. of hydroquinone are added to the solution, which is then stirred at 80° C. for 30 hours. The completion of cycloaddition is verified by the disappearance of the peak at $\lambda_{max}=305$ nm in the UV spectrum. The reaction mixture is evaporated in vacuo. The evaporation residue is dissolved in 150 ml. of benzene and washed with 30 ml. of water. The benzene solution is dried over magnesium sulfate and evaporated in vacuo. The crude product is chromatographed on a Kieselgel 60 (0.063–0.2 mm) column, using a 10:1 mixture of toluene and ethyl acetate as an eluent.

Yield: 14 g. (23.2%)
Melting point: 68° C.
t.l.c. (Kieselgel 60 plate, eluent: 10:1 benzene/ethyl acetate, development in iodine vapor): $R_f=0.6$ NMR spectrum: 5.2 ppm (s benzyl —CH$_2$—); 6.5 ppm (m olefin H-s), 7.4 ppm. (aromatic H-s).

PREPARATION EXAMPLE 5

2-Benzyloxycarbonyl-7-bromo-7-methoxycarbonyl-2-azabicyclo-[2.2.2]oct-5-ene

To 40 g. (0.2 moles) of N-benzyloxycarbonyl-1,2-dihydropyridine prepared as described in Preparation Example 3, 38 g. (0.23 moles) of freshly prepared methyl α-bromo-acrylate and 2 g. of hydroquinone are added. The reaction mixture is allowed to stand at room temperature for 48 hours, under protection from light. The completion of the cycloaddition is shown by the disappearance of the $\lambda_{max}==305$ nm from the UV spectrum. The reaction mixture is evaporated to an oily residue in vacuo, on a water bath of 40°–50° C., and extracted from three 40-ml. portions of a benzene/brine mixture. The benzene phase is dried over magnesium sulfate and evaporated in vacuo, whereupon it is column chromatographed on a 30-fold amount of Kieselgel (0.063–0.2 mm), using a 10:1 mixture of benzene and ethyl acetate for the elution.

Yield: 8 g. (0.01 moles), 11% based on the starting pyridine t.l.c. (Kieselgel 60 $F_{254}$, Merck Art. 5735; eluent: 10:1 benzene/ethyl acetate): $R_f=0.75$ IR spectrum (film) $cm^{-1}$: 1740 C=O; 1700 N—C=O, 1405 and 705 monosubstituted phenyl, 1250 —O—CH$_3$.

NMR spectrum (CDCl$_3$) ppm: 7.3 [s, Ar(t$^5$)]; 6.4 (m H$^5$, H$_1^6$); 5.2 (benzyl CH$_2$); 4.05 (m, H$_1^1$) 3.65 (OCH$_3$ s).

PREPARATION EXAMPLE 6

N-Ethoxycarbonyl-7-chloro-7-cyano-2-azabicyclo[2.2.2]-oct-5-ene

Following the procedure described Preparation Example 3 but using 19.1 ml. (21.7 g., 0.2 moles) of ethoxycarbonyl chloride instead of benzyloxycarbonyl chloride, N-ethoxycarbonyl-1,2-dihydropyridine is prepared, which is then further treated as described in Preparation Example 4. The title compound is obtained.

NMR spectrum: 6.56 and 6.63 (m, 5H and 6H); 3.08 ppm (m, 4H).

Yield: 11.8 g. (24.6%).

PREPARATION EXAMPLE 7

7-chloro-7-methoxycarbonyl-2-azabicyclo[2.2.2]oct-5-ene hydrobromide.

10 g. (0.03 moles) of 7-chloro-7-methoxycarbonyl-2-azabicyclo[2.2.2]oct-5-ene prepared according to Preparation Example 3 are dissolved in a mixture of 60 ml. of glacial acetic acid and 30 ml. of a 4–5N solution of hydrogen bromide in glacial acetic acid. The mixture is allowed to stand at room temperature for 10 minutes, and is then evaporated. The evaporation residue is dissolved in 5 ml. of acetone and 300 ml. of ether are added to the solution. The precipitated crystalline material is filtered off.

Yield: 8. g. (94%).

Melting point: 188° C.

IR spectrum: 1720 cm$^{-1}$ ester C=O.

NMR spectrum: 3.75 ppm (s —OCH$_3$); 6.2–6.5 ppm (olefin H-s).

PREPARATION EXAMPLE 8

7-Chloro-7-cyano-2-azabicyclo[2.2.2]oct-5-ene hydrogen bromide 5.0 g. (0.0165 moles) of N-benzyloxycarbonyl-7-chloro-7-cyano-2-azabicyclo[2.2.2]oct-5-ene are dissolved in a mixture of 30 ml. of glacial acetic acid and 15 ml. of a 4–5N glacial acetic acid/hydrogen bromide mixture. The reaction mixture is allowed to stand at room temperature for 10 minutes, and is then evaporated. The evaporation residue is crystallized from acetone.

Yield: 2.0 g. (0.0081 moles) 49%

Melting point: 224° to 226° C.

IR spectrum: 2220 cm$^{-1}$ C≡N

NMR spectrum (DMSO, d$_6$): 4.5 ppm (d H$_1^1$); 5.8–6.6 (m H$_5^1$+H$_6^1$).

PREPARATION EXAMPLE 9

4-Ethyl-7-chloro-7-methoxycarbonyl-2-azabicyclo[2.2.2]-oct-5-ene hydrobromide 16 g. (0.044 moles) of N-benzyloxycarbonyl-7-chloro-7-methoxycarbonyl-2-azabicyclo[2.2.2]oct-5-ene are dissolved in a mixture of 57 ml. of glacial acetic acid and 114 ml. of a 5N solution of hydrogen bromide in glacial acetic acid. The reaction mixture is allowed to stand at room temperature for a half to one hour. The progress of the reaction is monitored by thin layer chromatography. The mixture is then evaporated in vacuo, on a water bath of 40°–50° C. The obtained oily product is triturated with ether and decanted. The residual oil is chromatographed on a Kieselgel 60 (0.0063–0.2 mm.) column, using a 8:4:2 mixture of benzene, chloroform and ethanol as an eluent. The products obtained at R$_f$=0.1 and R$_f$=0.2, respectively, are collected. The two products differ in the configuration of the carbomethoxy group.

Yield: 7.2 g. (53%)

t.l.c. (Kieselgel 60 F$_{254}$; eluent: 10:1 benzene/acetone; development in iodine vapor): R$_f$=0.6. Under the same conditions, except that the eluent is a 8:4:2 mixture of benzene, chloroform and ethanol: R$_f$=0.1 and 0.2.

PREPARATION EXAMPLE 10

4-Ethyl-7-chloro-7-cyano-2-azabicyclo[2.2.2]oct-5-ene hydrobromide 1 g. of N-benzyloxycarbonyl-4-ethyl-7-chloro-7-cyano-2-azabicyclo[2.2.2]oct-5-ene are dissolved in a mixture of 2 ml. of glacial acetic acid and 0.1 ml. of a 5.3N solution of hydrogen bromide in glacial acetic acid. The mixture is allowed to stand at room temperature for half an hour, under exclusion of moisture. The mixture is evaporated in vacuo on a water bath of 40° C., and three-times 20 ml. of acetone and then two-times 10 ml. of methanol are evaporated off. The evaporation residue contains in addition to the desired product also the corresponding acid, obtained by hydrolysis of the cyano group. The two products are separated on a Kieselgel 60 (0.063–0.2 mm.) column, using a 8:4:2 mixture of benzene, chloroform and ethanol as an eluent.

Yield: 0.1 g. (0.00035 moles, 12%) of the title compound.

t.l.c. (Kieselgel 60 F$_{254}$; eluent; a 8:4:2 mixture of benzene, chloroform and ethanol): R$_f$ acid=0.14; R$_f$ nitrile=0.44.

IR spectrum (KBr) cm$^{-1}$: 3330 NH, 2300 C≡N.

NMR spectrum (CDCl$_3$ ppm: 6.1 (m H$_1^5$+H$_1^6$); 4.2 (d, H$_1^1$); 1.2 (t ethyl CH$_3$).

PREPARATION EXAMPLE 11

7-Bromo-7-methoxycarbonyl-2-azabicyclo[2.2.2]oct-5-ene hydrobromide 8.0 g. of N-benzyloxycarbonyl-7-bromo-7-methoxycarbonyl-2-azabicyclo[2.2.2]oct-5-ene are dissolved in 40 ml of dichloromethane, and the solution is saturated with hydrogen bromide gas under cooling for five minutes. After saturation the mixture is allowed to stand for another five minutes, whereupon it is evaporated to yield an oily residue, which is then crystallized from acetone.

Yield: 4.0 g. (0.0125 moles, 60%).

t.l.c. (Kieselgel 60 F$_{254}$; eluent: a 8:4:2 mixture of benzene, chloroform and ethanol: development in iodine vapor); R$_f$=0.55.

IR spectrum (KBr) cm$^{-1}$: 1740 C=O; 1250 OCH$_3$.

PREPARATION EXAMPLE 12

6-Chloro-6-methoxycarbonyl-2-azabicyclo[2.2.2]octane hydrobromide 8.5 g. (0.03 moles) of 7-chloro-7-methoxycarbonyl-2-azabicyclo[2.2.2]oct-5-ene hydrobromide are dissolved in 85 ml. of methanol. 0.85 g. of a 10% palladium-on-charcoal catalyst are prehydrogenated in 15 ml. of methanol, and a clear solution of the starting material to be hydrogenated is added in a closed system. Hydrogenation is carried out in a closed system, the progress of the reaction is monitored by measuring the hydrogen consumption. When the calculated amount of hydrogen is used up, the reaction is terminated. When the reaction is not terminated timely, the reaction proceeds further and the chlorine is replaced by hydrogen. The catalyst is filtered off, the solution is evaporated. A crystalline material is obtained, which is triturated in about 20 ml. of acetone, and allowed to stand overnight in a refrigerator. The precipitate is filtered off on the next day, pulpified with two 5-ml. portions of cold acetone, and dried.

Yield: 7 g. (0.0244 moles, 82%).
Melting point: 181° to 183° C.

PREPARATION EXAMPLE 13

N-[2-(3'-Indolyl)-ethyl]-7-chloro-7-methoxycarbonyl-2-azabicyclo[2.2.2]oct-5-ene 6.0 g. (21.2 mmoles) of 7-chloro-7-methoxycarbonyl-2-azabicyclo[2.2.2]oct-5-ene hydrobromide. 6.0 g. (27 mmoles) of tryptophyl bromide and 25 ml. (18.0 g., 0.18 moles) of triethyl amine are dissolved in 80 ml. of absolute methanol. The solution is allowed to stand at room temperature for one day. The progress of the reaction is monitored by thin layer chromatography, using a Kieselgel 60 plate, 10:2 mixture of toluene and ethyl acetate as an eluent, and carrying out the development in iodine vapor. $R_f$ product: 0.5.

The reaction mixture is evaporated in vacuo. To the evaporation residue 300 ml. of ethyl acetate are added, adn the precipitated solid triethyl amine hydrobromide is filtered off. The mother liquor is evaporated. The obtained evaporation residue, which is about 7 g. of an oily product, is crystallized from a mixture of 50 ml. of ethyl acetate and 2-3 ml. of n-hexane. The mother liquor of the product is subjected to column chromatography on a Kieselgel 60 (0.063-0.2 mm.) column, using a 10:1 mixture of toluene and ethyl acetate as an eluent, and the product is crystallized from a mixture of n-hexane and ethyl acetate as described hereinabove.

Yield: 3.5 g. (48.6%)
Melting point: 128°-130° C.
IR spectrum (KBr): 1720 cm$^{-1}$ ester C=O, 3400 cm$^{-1}$ indole N—H
NMR spectrum, ppm: 7.9 (indole N—H); 7.6 (m aromatic H); 6.2-6.5 (m, $H_1^5+H_1^6$); 3.8 (s —OCH$_3$).

PREPARATION EXAMPLE 14

N-[2-(3'-Indolyl)-ethyl]-7-chloro-7-cyano-2-azabicyclo[2.2.2]oct-5-ene 0.9 g. of tryptophyl bromide are dissolved in 20 ml. of absolute acetonitrile, and 1.0 g. (0.00403 moles) of 7-chloro-cyano-2-azabicyclo[2.2.2]oct-5-ene hydrobromide and 2.4 ml. of absolute triethyl amine are added to the solution. The homogeneous solution obtained is stirred for 3 days, under exclusion of light and moisture. The progress of the reaction is monitored by thin layer chromatography. On a Kieselgel 60 $F_{254}$ plate, using a 10:1 mixture of benzene and acetone as an eluent, $R_f$ tryptophyl bromide is 0.86, $R_f$ product is 0.76. The reaction mixture is evaporated in vacuo, on a water bath of 30° to 40° C. The evaporation residue is dissolved in 15 ml. of ether, and extracted with two 5-ml. portions of aqueous ammonia (pH=10). The ethereal phase is dried over magnesium sulfate, and evaporated in vacuo. The obtained oily product is crystallized from 3 ml. of methanol.

Yield: 0.71 g. (0.002324 moles), 55%.
Melting point: 126° to 128° C.
t.l.c. (Kieselgel 60 $F_{254}$: eluent: 10:1 benzene/acetone; development: in UV light of 254 nm or in iodine vapor) $R_f$=0.76

IR spectrum (KBr) cm$^{-1}$: 2300 C≡N, 3300 indole NH
NMR spectrum (CDCl$_3$) ppm: 3.8 (d, $H_1^1$), 6.2-6.8 (m $H_1^5+H_1^6$), 7.05-7.7 (m Ar H+indole $H_1^2$).

PREPARATION EXAMPLE 15

N-[2-(3'-Indolyl)-ethyl]-6-chloro-6-methoxycarbonyl-2-azabicyclo[2.2.2]octane.

3.84 g. (0.013 moles) of 3-chloro-6-methoxycarbonyl-2-azabicyclo[2.2.2]octane hydrobromide, 3.05 g. of tryptophyl bromide and 5.55 g. (0.052 moles, 7.6 ml.) of triethyl amine are dissolved in 35 ml. of absolute methanol, and the solution is allowed to stand at room temperature for two days. The reaction mixture is evaporated, and to the evaporation residue a mixture of 70 ml. of benzene and 35 ml. of water is added. The organic phase is separated, and washed with two 15-ml. portions of water. The combined aqueous phases are extracted with 15 ml. of benzene. The combined benzene phases are dried over magnesium sulfate, decolored with charcoal, and evaporated in vacuo. From the evaporation residue 25 ml. of ethanol are eliminated by evaporation, and the residual solid is crystallized from 3 ml. of ethanol. The mother liquor is evaporated, and the residue is crystallized from isopropanol.

Yield: 1.5 g (0.0043 moles), 33%.

PREPARATION EXAMPLE 16

N-[2-(3'-Indolyl)-ethyl]-4-ethyl-7-chloro-7-methoxycarbonyl-2-azabicyclo[2.2.2]oct-5-ene 10.3 g. (0.033 moles) of 4-ethyl-7-chloro-7-methoxycarbonyl-2-azabicyclo[2.2.2]oct-5-ene, 7.4 g. (0.033 moles) of tryptophyl bromide and 19 ml. of triethyl amine are dissolved in 80 ml. of absolute methanol. The reaction is carried out at room temperature and monitored by thin layer chromatography (Kieselgel 60 $F_{254}$ plate) until tryptophyl bromide is completely used up, using a 10:1 mixture of benzene and acetone as an eluent, and a new product can be detected with a 8:4:2 mixture is benzene, chloroform and ethanol. The reaction mixture is evaporated in vacuo. To the residual oil 100 ml. of water are added, and the obtained mixture is extracted with three 100-ml. portions of benzene. The combined benzene phases are dried over magnesium sulfate, filtered and evaporated. If according to t.l.c. the reaction mixture does not contain any decomposition product, the desired product is crystallized from a 96% ethanol. If the reaction mixture is contaminated with by-products due to decomposition, the crude product is purified by column chromatography.

Yield: 3.8 g. (1.0 mmole) 31%.
t.l.c. (Kieselgel 60 $F_{254}$; eluent: 10:1 mixture of benzene and acetone and 8:4:2 mixture of benzene, chloroform and ethanol, resp.; development: in UV light of 254 nm or in iodine vapor): $R_f$: 0.75.
IR spectrum, cm$^{-1}$: 3300 indole NH, 1720 ester C=O.
NMR spectrum (CDCl$_3$) ppm: 6.2-6.8 (m $H_1^5+H_1^6$), 7.05-7.7 (m Ar+indole $H_1^2$), 3.8 (d $H_1^1$).

PREPARATION EXAMPLE 17

N-[(3'-Indolyl)-acetyl]-7-chloro-7-methoxycarbonyl-2-azabicyclo[2.2.2]oct-5-ene 5.8 g. (0.03 moles) of indolyl-3-acetic acid and 4.6 ml. (3.3 g., 0.033 moles) of triethyl amine are dissolved in 97 ml. of dimethyl formamide. The solution is cooled to −5° C. to −10° C., and 4.1 ml. (4.1 g., 0.034 moles) of pivalyl chloride are added dropwise, at the above temperature. After stirring for 20 minutes a thick suspension is obtained. To the suspension a solution of 8.0 g.) 0.0284 moles) of 7-chloro-7-methoxycarbonyl-2-azabicyclo[2.2.2]oct-5-ene hydrobromide and 4.6 ml. (3.3 g., 0.033 moles) of triethyl amine in 97 ml. of dimethyl formamide is added at a temperature between 0° C. and −5° C. The reaction mixture is then allowed to warm up to room temperature, and stirred for an additional hour. The precipitated triethyl amine hydrochloride and hydrobromide, resp. is filtered off and washed with 5 ml. of dimethyl formamide. The mother liquor is evaporated in vacuo. The evaporation residue is dissolved in 400 ml. of ethyl acetate, washed with two 40-ml. portions of water, and dried over sodium sulfate. The ethyl-acetate solution is evaporated, and the precipitated crystalline product is filtered off. Yield: 8.5 g. The crude product is dissolved in a mixture of 250 ml. of chloroform and 60 ml. of methanol and solution is evaporated. The precipitated crystalline product is filtered off and washed with 10 ml. of chloroform.

Yield: 8.1 g. (0.0226 moles), 68%.

Melting point: 201°–202° C.

IR spectrum (KBr) cm$^{-1}$: ester C=O 1720, acid amine C=O 1640.

NMR spectrum: 7.0–7.7 ppm; indole aromatic; 5.8 and 6.4 ppm: m ($H_5^1 + H_6^1$) 3.75 ppm (s—OCH$_3$).

Mass spectrum m/z: M=358, 322, 301, 299, 238, 157, 130, 121, 119, 117, 103, 93, 91, 81, 80, 77.

PREPARATION EXAMPLE 18

N-[(3'-Indolyl)-acetyl]-7-chloro-7-cyano-2-azabicyclo-[2.2.2]oct-5-ene

Following the procedure described in Preparation Example 17 but starting from 8.0 g. (0.032 moles) of 7-chloro-7-cyano-2-azabicyclo[2.2.2]oct-5-ene hydrogen bromide, the title compound is obtained.

Yield: 4.65 g. (0.0143 moles) 44.6%.

Melting point: 176° C.

IR spectrum (IBr): acid amide C=O 1640 cm$^{-1}$, cyano 2230 cm$^{-1}$

NMR spectrum: 7.0–7.7 ppm, indole aromatic, 6.6 m ($H_5^1 + H_6^1$).

Mass spectrum m/z: M=325, 389, 238, 158, 157, 130, 121, 117, 116, 103, 102, 93, 81, 80, 77.

t.l.c. (Kieselgel 60 F$_{254}$ plate, eluent: 10:1 mixture of chloroform and methanol, development in UV light of 254 nm or idoine vapor): R$_f$=0.7.

PREPARATION EXAMPLE 19 CL

N-[(3'-Indolyl)-acetyl]-6-chloro-6-methoxycarbonyl-2-azabicyclo[2.2.2]octane 7.1 g. of 3-indolyl-acetic acid, 4.2 g. (0.04 moles), 5.75 ml. of triethyl amine are dissolved in 120 ml. of absolute dimethyl formamide. The solution is cooled to a temperature between −5° C. and −10° C., and 4.8 g. (0.04 moles) 4.9 ml.) of pivalyl chloride are added dropwise, at the same temperature. After stirring for 20 minutes a thick suspension is obtained, to which a solution of 11.4 g. (0.04 moles) of 6-chloro-6-methoxy-carbonyl-2-azabicyclo[2.2.2]octane hydrobromide and 4.2 g. (0.04 moles) of triethyl amine in 120 ml. of dimethyl formamide is added, between 0° C. and −5° C. When the addition is complete, the mixture is stirred at room temperature for an additional hour. The precipitated solid, which is triethyl amine hydrochloride or hydrobromide, is filtered off and washed with a small amount of dimethyl formamide. The mother liquor is evaporated in a vacuo of 10 to 20 torr, on a bath of 60° C. To the evaporation residue 400 ml. of ethyl acetate are added, and the mixture is washed with two 40-ml. portions of water, 60 ml. of a 5% sodium bicarbonate solution and finally 60 ml. of a 20% sodium chloride solution, dried over magnesium sulfate, and evaporated. The evaporation residue is recrystallized from 300 ml. of ethanol.

Yield: 9.3 g. (0.026 moles), 65%

Melting point: 195°–196° C.

PREPARATION EXAMPLE 20

N-[(3'-Indolyl)acetyl]-7-bromo-7-methoxycarbonyl-2-azabicyclo[2.2.2]oct-5-ene 2.2 g. (0.0126 moles) of 3-indolyl-acetic acid are dissolved in 30 ml. of absolute dimethyl formamide. 1.2 g. of triethyl amine are added to the solution, which is then cooled to −5° C. to −10° C. At this temperature 1.6 g. (0.0126 moles) of pivalyl chloride are added dropwise under vigorous stirring. The triethyl amine hydrochloride immediately precipitates from the solution. After stirring for 20 minutes a solution of 4.0 g. (0.0126 moles) of 7-bromo-7-methoxy-carbonyl-2-azabicyclo[2.2.2]-oct-5-ene hydrobromide and 1.2 g. of triethyl amine in 20 ml. of dimethyl formamide is added. The mixture is stirred at room temperature for an additional hour, and the hydrochloride of hydrobromide of the precipitated triethyl amine is filtered off. The mother liquor is evaporated in vacuo, on an oil bath of 60° C. The evaporation residue is dissolved in 300 ml. of dichloromethane and washed with 100 ml. of water. The dichloromethane phase is dried over magnesium sulfate, and evaporated in vacuo. The evaporation residue is crystallized from acetone.

Yield: 2.0 g. (0.005 moles) 40%.

t.l.c. (Kieselgel 60 F$_{254}$, eluent: a 8:4:2 mixture of benzene, chloroform and ethanol, development: in UV light of 254 nm or in iodine vapor) R$_f$=0.85.

IR spectrum (KBr) cm$^{-1}$: 3250 NH, 1720 ester C=O, 1620 N—C=O.

NMR spectrum (CDCl$_3$+DMSO d$_6$) ppm: 7.7–7.3 indole aromatic, 6.6 m ($H_1^5 + H_1^6$), 5.0 (m $H_1^1$).

The new compounds of the Formulae (II) and/or (III) are valuable in the treatment of ulcers caused by the secretion of gastric acid as the new compounds have the ability to inhibit the secretion of gastric acid.

The preferred method of administration of the new compounds to a patient in need of antiulcer therapy is oral administration and the preferred dosage range is 10 to 100 mg per day for the patient.

Preferably the new compounds of the Formulae (II) and/or (III) are administered in the form of a pharmaceutical composition which contains a pharmaceutically effective amount of the compound of the Formulae (II) and/or (III) along with a pharmaceutically acceptable inert carrier or excipient.

It has been found that the compound methyl 1,3-vinylene-1,3,4,6,7,12b-hexahydro-2H,12H-indolo[2,3-a]quinolizinyl-1-carboxylate in rats has an ED$_{50}$ value of 25 mg/kg i.p. and an LD$_{50}$ in rats of 250 mg/kg i.p.

It has been found that the compound 2-cyano-3a,4,6,7,12b,12c-hexahydro-3H,12H-indolo[2,3-g]-cyclopent[a]indolizine has an ED$_{50}$ value of 20 mg/kg i.p. and an LD$_{50}$ value of 200 mg/kg i.p.

The gastric acid secretion inhibition activity was determined by the method of Shay, *Gastroenterology,* 19845, 5, 43–46.

We claim:

1. Compounds of the formula (II),

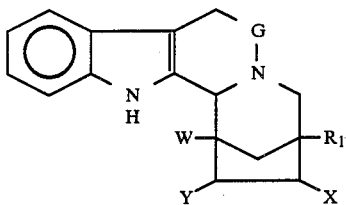

in which

W is alkoxycarbonyl having from one to four carbon atoms in the alkoxy moiety or cyano, $R_1$ is hydrogen or alkyl having from one to four carbon atoms, G is a >CH$_2$ or >C=O group, and X and Y each stands for hydrogen or together represent a C—C bond.

2. Compounds of the formula (III),

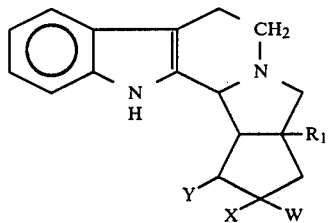

in which

W is alkoxycarbonyl having from one to four carbon atoms in the alkoxy moiety or cyano, $R_1$ is hydrogen or alkyl having from one to four carbon atoms, and X and Y each stands for hydrogen or together represent a C—C bond.

3. Methyl 1,3-vinylene-1,3,4,6,7,12b-hexahydro-2H,12H-indolo[2,3-a]quinolizinyl-1-carboxylate as defined in claim 1.

4. 2-cyano-3a,4,6,7,12b,12c-hexahydro-3H,12H-indolo(2,3-g)-cyclopent(a)indolizine as defined in claim 2.

5. An antiulcer pharmaceutical composition which comprises a pharmaceutically effective amount of the compound of the Formula (II) as defined in claim 1 in association with a pharmaceutically acceptable inert carrier.

6. An antiulcer pharmaceutical composition which comprises a pharmaceutically effective amount of the compound of the Formula (III) as defined in claim 2 in association with a pharmaceutically acceptable inert carrier.

7. A method of treating ulcers in an animal subject which comprises the step of administering to said animal subject a pharmaceutically effective amount of the compound of the Formula (II) as defined in claim 1.

8. A method of treating ulcers in an animal subject which comprises the step of administering to said animal subject a pharmaceutically effective amount of the compound of the Formula (III) as defined in claim 2.

* * * * *